United States Patent [19]

Huang et al.

[11] Patent Number: 4,937,340
[45] Date of Patent: Jun. 26, 1990

[54] HIGH ENERGY INSENSITIVE CYCLIC NITRAMINES

[75] Inventors: Der-Shing Huang, Carmichael; Renato R. Rindone, Fair Oaks, both of Calif.

[73] Assignee: Aerojet-General Corporation, Folsom, Calif.

[21] Appl. No.: 320,143

[22] Filed: Mar. 7, 1989

[51] Int. Cl.$^5$ ............... C07D 251/00; C07D 251/18; C07D 251/48
[52] U.S. Cl. ........................... 544/194; 149/92
[58] Field of Search ............ 544/194, 196, 204

[56] References Cited

U.S. PATENT DOCUMENTS 4,562,188 12/1985 Kuhla et al. ............... 544/204

Primary Examiner—Mary C. Lee
Assistant Examiner—J. Richter
Attorney, Agent, or Firm—Townsend and Townsend

[57] ABSTRACT

Cyclic nitramines of the formula

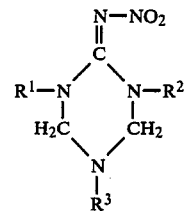

in which $R^1$, $R^2$ and $R^3$ are independently selected from the group consisting of H, NO and $NO_2$, and acid salts of the compound in which $R^1$, $R^2$ and $R^3$ are each H, are disclosed. These compounds are useful as components in energetic compositions, including rocket and gun propellants and explosives, and are of particular interest due to their combination of high energy output and insensitivity. Compounds in which $R^3$ is H or NO are further useful as intermediates in the preparation of those in which $R^3$ is $NO_2$. Also disclosed is a method for producing such compounds involving the reaction between hexamethylenetetramine and nitroguanidine.

10 Claims, No Drawings

HIGH ENERGY INSENSITIVE CYCLIC NITRAMINES

BACKGROUND OF THE INVENTION

This invention relates to energetic munitions compounds, and in particular to cyclic nitramines.

The propellant industry is constantly striving for compounds that are both safe and have adequate performance characteristics for use in munitions, including both explosives and propellants. Some current high volume ingredients such as cyclotrimethylenetrinitramine (RDX) are very effective in providing impetus for projectiles. However, this compound and others like it are sensitive to shock and electric spark. Other less hazardous compounds such as nitroguanidine (NQ), for example, can be substituted for RDX. Unfortunately, nitroguanidine, despite having excellent spark and shock insensitivity, suffers in the performance aspect when compared with RDX. To date, there is no known cost effective compound which is both safe to handle and has performance characteristics adequate to replace the high volume energetic compounds.

SUMMARY OF THE INVENTION

A novel class of cyclic nitramines including acid salts of one member of the class, has now been developed. These compounds are characterized by both insensitivity and high performance. Certain members of this class are intermediates for the manufacture of other members of the class, and novel procedures have also been developed for the preparation of these compounds.

The compounds themselves offer advantages over known energetic compounds in a variety of uses. In air-augmented systems, these compounds provide a higher impulse due to an inherently higher fuel ratio, as well as a higher degree of safety. They can also be used to advantage in gun propellants to produce a lower barrel temperature for a given impulse. Their high impulse and increased safety are likewise of benefit in rocket propellants and explosives.

DETAILED DESCRIPTION OF THE INVENTION

The cyclic nitramines of the present invention are those having the formula:

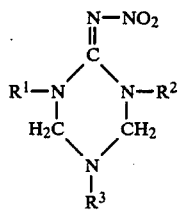

in which $R^1$, $R^2$ and $R^3$ are independently selected from the group consisting of H NO and NO2. The term "independently selected" is used herein to denote that any two or all three of the substituents may be identical. While all of these compounds have activity as energetic compounds, those in which $R^3$ is H or NO also have utility as intermediates in the manufacture of those in which $R^3$ is NO2. The conversion of these intermediates to the nitroso and nitro analogs is described below.

Acid salts of the compound in which $R^1$, $R^2$ and $R^3$ are each H (i.e., 2-nitroiminohexahydro-1,3,5-triazine) are also included within the present invention. Examples of acid salts within the scope of the invention are salts formed with hydrohalic acids, sulfuric acid, phosphoric acid, acetic acid and nitric acid. The preferred hydrohalic acid is hydrochloric acid. The acid salts will generally contain one equivalent of acid per mole of the 2-nitroiminohexahydro-1,3,5-triazine.

Examples of specific compounds within the formula are those in which $R^1$, $R^2$ and $R^3$ are as follows (Table I):

TABLE I

ILLUSTRATIVE COMPOUNDS

| | $R^1$ | $R^2$ | $R^3$ | Name |
|---|---|---|---|---|
| (I) | H | H | H | 2-nitroimino-hexahydro-1,3,5-triazine (and acid salts thereof) |
| (II) | H | H | NO | 2-nitroimino-5-nitroso-hexahydro-1,3,5-triazine |
| (III) | H | H | NO2 | 2-nitroimino-5-nitro-hexahydro-1,3,5-triazine |
| (IV) | NO | H | NO2 | 2-nitroimino-3-nitroso-5-nitro-hexahydro-1,3,5-triazine |
| (V) | NO2 | H | NO2 | 2-nitroimino-3,5-dinitro-hexahydro-1,3,5-triazine |
| (VI) | NO | NO | NO2 | 2-nitroimino-1,3-dinitroso-5-nitro-hexahydro-1,3,5-triazine |
| (VII) | NO2 | NO2 | NO2 | 2-nitroimino-1,3,5-trinitro-hexahydro-1,3,5-triazine |

Within the scope of the general formula given above, certain embodiments are preferred. These include compounds in which $R^3$ is NO2; and compounds in which $R^1$ and $R^2$ are H; and compounds in which $R^1$ is NO2 and $R^2$ is H.

These compounds may be prepared by the use of a Mannich-type reaction, followed by nitration to achieve the desired final product.

The novel method provided as part of the present invention, however, involves the reaction of hexamethylenetetramine with nitroguanidine to produce 2-nitroimino-hexahydro-1,3,5-triazine. The surprising nature of this novel method originates in the discovery that 2-nitroimino-hexahydro-1,3,5-triazine cannot be directly formed by the reaction of nitroguanidine with ammonia and formaldehyde. The 2-nitroimino-hexahydro-1,3,5-triazine is however formed by the reaction of nitroguanidine with hexamethylenetetramine. The reaction is conducted in an acidic reaction medium. Examples of acidic reaction media suitable for the reaction are aqueous hydrochloric, sulfuric, phosphoric, nitric and acetic acids. The preferred medium is concentrated aqueous hydrochloric acid. The reaction may be conducted under ambient conditions of temperature and pressure. The product precipitates, and is recovered from the reaction mixture by conventional techniques. To produce nitro-analogs of this compound, nitration with conventional nitrating agents is then performed in accordance with conventional nitration procedures, with higher degrees of nitration resulting in the various compounds listed in Table I above. Suitable nitrating agent include nitric acid and mixtures of nitric acid and sulfuric acid.

The compound where $R^3$ is NO and $R^1$ and $R^2$ are H is formed by the reaction of 2-nitroimino-hexahydro-1,3,5-triazine acid salt with a nitrosating agent such as sodium nitrite in the presence of HCl. This compound may serve as an intermediate in the preparation of the compound where $R^3$ is $NO_2$, which is formed by nitrolysis of the former with nitric acid. An alternative and more cost effective route to the nitro analog is to treat the hydrochloride salt of 2-nitroimino-hexahydro-1,3,5-triazine with a mixture of concentrated nitric and sulfuric acids to form the nitro analog directly, avoiding the need to prepare the intermediate and thereby eliminating a step from the procedure.

The following examples are offered for purposes of illustration and are intended neither to limit nor define the invention in any manner.

EXAMPLE 1

This example illustrates the preparation of 2-nitroimino-hexahydro-1,3,5-triazine hydrochloride. Compound I of the above table in the hydrochloride form, using the novel method of the present invention.

A three-neck 1000-mL flask fitted with a condenser, a magnetic stirrer a thermometer, and a positive nitrogen atmosphere was charged with 750 mL of aqueous HCl (37.0-38.0 weight %). Nitroguanidine (41.25 g. 0.396 mole) was then added in one portion, requiring approximately thirty minutes to dissolve. Hexamethylenetetramine (100 g. 0.713 mole) was then added in several portions over twenty minutes, during which time an exotherm occurred, raising the reaction temperature from 21° to 38° C. Upon completion of the hexamethylenetetramine addition, the reaction mixture became clear and colorless and was stirred at ambient temperature overnight. The product precipitated out as a white powder, and was filtered, washed with 100 mL of methanol, and dried in vacuo (60°-65° C. 0.5 mm Hg). The resulting product weighed 51.62 g (71.7% yield), with m.p. 189° C. (with decomposition): an equivalent weight of 180.8 (by $AgNO_3$ titration) as compared with a theoretical value of 181.58 and a value of 186.3 by NaOH titration; chloride content 19.62 weight %, as compared with a theoretical value of 19.52 weight %. The structure was confirmed as that of Compound I by proton NMR and FTIR as follows:

proton NMR ($d^6$-DMSO): $\delta$8.9 (s, —NHC=NH—), $\delta$4.2 (s, —NHCH$_2$NHCH$_2$NH—)

FTIR (KBr): 3250 cm$^{-1}$, 3212 cm$^{-1}$ (NH stretch), 3000-2600 cm$^{-1}$ (salt of secondary amine), 1582 cm$^{-1}$ ($NO_2$ asymmetric. C-N stretch)

DSC (differential scanning calorimetry) indicated an exotherm onset at 182° C. and an exotherm peak at 195° C. Elemental analysis was as follows: calculated for $C_3H_8Cl_1N_5O_2$: C, 19.84; H, 4.44; N, 38.57; Cl, 19.52; found: C, 19.58; H, 4.47; N, 38.54; Cl, 19.73.

EXAMPLE 2

This example illustrates the preparation of 2-nitroimino-5-nitroso-hexahydro-1,3,5-triazine, Compound II above.

A three-neck 250-mL flask fitted with a mechanical stirrer, thermometer, a condenser, an addition funnel, and a positive nitrogen atmosphere was charged with sodium nitrite (4.29 g, 62.17 mmoles) and deionized water 165 mL. The solution was chilled to 5° C. in an ice bath. A 3.0 g (16.52 mmoles) portion of the product of Example 1 was added in one portion. Dilute hydrochloric acid solution (63 mL) was added dropwise over fifteen minutes at 3.2°-4.5° C. The resulting white slurry mixture was stirred at 1.2°-3.2° C. for 2.63 hours at ambient temperature (15° C.) overnight. An off-white product was formed, and was filtered off, washed with deionized water (75 mL). and dried in vacuo (60°-65° C. 0.5 mm Hg). The final product weighed 2.73 g (94.9% yield), with m.p. 193° C. (with decomposition): and equivalent weight (theory. 174.12) 167.1. The structure was confirmed as that of Compound II by proton NMR and FTIR as follows:

proton NMR ($d^6$—DMSO): $\delta$9.2. 8.7 (s, —NHC=NH—), $\delta$5.4, 4.7 (s, —NHCH$_2$NHCH$_2$NH—)

FTIR (KBr): 3275 cm$^{-1}$, 3149 cm$^{-1}$ (NH stretch), 1620 cm$^{-1}$ ($NO_2$ asymmetric, C-N stretch)

DSC indicated an exotherm onset at 190° C. and an exotherm peak at 206° C.

EXAMPLE 3

This example illustrates the preparation of 2-nitroimino-5-nitro-hexahydro-1,3,5-triazine. Compound III above.

A three-neck 50-mL flask fitted with a magnetic stirrer, thermometer, a condenser, and a positive nitrogen atmosphere was charged with 10 mL 99% nitric acid. The solution was chilled to $-26.5°$ C. in an ethylene dichloride/dry ice bath. A 0.76 g (4.36 mmol2es) portion of the product of Example 2 wa added in several portions over eleven minutes. Following the addition, the reaction mixture was maintained at $-22°$ C. to $-28°$ C. for thirty minutes, followed by 2°-3° C. for one hour, and then quenched with 102 g ice. A blue-colored mixture resulted following the quench, turning to a white slurry mixture after stirring for a few minutes in air. An off-white product was filtered, washed with deionized water, and dried in vacuo (60°-65° C., 0.5 mm Hg). The product weighed 0.76 g (91.6% yield), with m.p. 207° C. (with decomposition), and equivalent weight (theory, 190.12) 191.8. The structure was confirmed as that of Compound III by proton NMR and FTIR as follows:

proton NMR ($d^6$-DMSO): $\delta$8.9 (s, —N/C=NH—), $\delta$5.0 (s, —NHCH$_2$NHCH$_2$NH—)

FTIR (KBr): 3330 cm$^{-1}$, 3216 cm$^{-1}$ (NH stretch), 3123 cm$^{-1}$ 3047 cm$^{-1}$, 2972 cm$^{-1}$ (CH stretch), 1607 cm$^{-1}$ $NO_2$ asymmetric, C-N stretch), 1572 cm$^{-1}$ ($NO_2$ asymmetric)

DSC indicated an exotherm onset at 213° C. and exotherm peak at 222° C. FAB/MS: (M+H) at m/e 191 for mol. wt. 190. Elemental analysis was as follows: calculated for $C_3H_6N_6O_4$: C, 18.95; H, 3.18; N, 44.20; found: C, 19.69; H. 3.22; N, 43.80.

EXAMPLE 4

This example illustrates the two-step method for preparing 2-nitroimino-5-nitro-hexahydro-1,3,5-triazine (Compound III) from 2-nitroimino-hexahydro-1,3,5-triazine hydrochloride (Compound I).

A three-neck 50 mL flask fitted with a magnetic stirrer, thermometer, a condenser, and a positive nitrogen atmosphere was charged with 320 mL concentrated nitric acid (90 weight percent, 6.86 moles). The flask was chilled to $-11°$ C. in an ethylene dichloride/dry ice bath. Concentrated sulfuric acid (96.9 g weight percent, 320 mL) was then added dropwise over thirteen minutes at $-2°$ C. to $-11°$ C., and the resulting mixture was cooled to $-15°$ C. A 95.5 g portion of the product of Example 1 (0.526 moles) was then added in several portions over approximately twenty minutes at $-13.5°$ C. to −16.5° C. The resulting mixture was a light yellow slurry, stirred at −17° C. to −22° C. for one hour, then warmed to 0° c. to 5° C. by switching to an ice bath. The slurry mixture became clear at a pot temperature of approximately −7° C. The reaction mixture was maintained at −3.6° C. for one hour, then quenched with 3000 g ice and 2000 mL deionized water. After the quench, white crystals of 2-nitroimino-5-nitro-hexahydro-1,3,5-triazine precipitated, and these were filtered and washed with 500 mL deionized water, dried in vacuo (65° C, 0.5 mm Hg) overnight. The final product weighed 94.5 g, representing a yield of 94.5%.

EXAMPLE 5

In Table II, calculated and observed thermochemical properties are given for two compounds within the scope of the invention (Compounds III and IV of Table I), as well as two known and widely used energetic compounds, nitroguanidine (NQ) and cyclonite (cyclo-1,3,5-trimethylene-2,4,6-trinitramine, RDX) for purposes of comparison. The figures for detonation velocity and detonation pressure were calculated using the method of Rothstein and Peterson and the Kamlet short method.

TABLE II
THERMOCHEMICAL PROPERTIES OF ENERGETIC COMPOUNDS
(Observed values indicated by asterisk; all others calculated)

|  | Compound III | Compound IV | NQ | RDX |
|---|---|---|---|---|
| Heat of Formation (kcal/mole) | 16.3* | 26.4 | −22.1* | 14.7* |
| Heat of Explosion (kcal/100 g) | −80.7 | −101 | −59.7 | −120 |
| Detonation Velocity (m/sec) | | | | |
| Rothstein-Peterson | 8380 | 9070 | 8270 | 8950 |
| Kamlet | 8220 | 8710 | 7660 | 8850 |
| Density (g/mL) | 1.79 | 1.88 | 1.58 | 1.91 |
| Density (g/mL) | 1.75* | — | 1.71* | 1.82* |
| Detonation Pressure (kbars) (Kamlet) | 299 | 346 | 267 | 350 |

EXAMPLE 6

The products of Examples 3 and 4 were subjected to a series of standard tests using industry accepted test procedures to determine hazard properties. The tests included Differential Scanning Calorimetry (DSC), Differential Thermal Analysis (DTA), Bureau of Mines Impact (2 kg weight), rotary friction and electric spark sensitivity. The test results are listed in Table III.

TABLE III
HAZARD PROPERTIES

|  | Example 3 | Example 4 |
|---|---|---|
| Impact (height in cm) | 80 (noise) | 95 (flash) |
| DTA (°C.) | | |
| Exotherm Onset | 182 | 201 |
| Exotherm Peak | 195 | 209 |
| DSC (°C.) | | |
| Exotherm Onset | 212.7 | 224.6 |
| Exotherm Peak | 221.7 | 226.6 |
| Rotary friction (g/2000 rpm) | >4000 | >4000 |
| Spark (joules) | >1.0 | >1.0 |

The cyclic nitramines of the present invention may be used as components of energetic compositions, in place of or in combination with other components known for use in such compositions. The term "energetic compositions" is intended to include explosive compositions, rocket propellant compositions and gun propellant compositions.

Referring to Table II, note that the compounds of the present invention combine favorable high positive heats of formation with high heats of explosion. These characteristics make the compounds excellent candidates for reducing flame temperature in gun propellant compositions, while increasing their impetus. The compounds of the present invention may also be utilized as substitutes for nitroguanidine in rocket propellants and explosive compositions to increase missile range or to improve explosion performance while improving the safety characteristics of the composition.

The compounds of the present invention may also be used as substitutes for RDX and HMX in explosive compositions to form insensitive explosives, i.e., explosives with low vulnerability ammunition (LOVA) properties. The hazard property test results listed in Example 6 above show that the tested compound is less sensitive to impact when compared with RDX while being thermally comparable to RDX.

To those skilled in the art, many modifications and variations of the present invention are possible in light of the above teachings. It is therefore to be understood that the present invention may be practiced otherwise than as specifically described herein and still be within the spirit and scope of the appended claims.

What is claimed is:

1. A compound having the formula

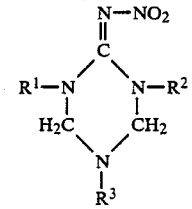

in which $R^1$, $R^2$ and $R^3$ are independently selected from the group consisting of H, NO and $NO_2$; and acid salts thereof for said compound where $R^1$ is H, $R^2$ is H and $R^3$ is H.

2. A compound in accordance with claim 1 in which $R^3$ is $NO^2$.

3. A compound in accordance with claim 1 in which $R^2$ is H.

4. A compound in accordance with claim 1 in which $R^1$ is H, $R^2$ is H, and $R^3$ is H; in which said compound is a member selected from the group consisting of the sulfate salt, the phosphate salt, the nitrate salt and the hydrohalide salt thereof.

5. A compound in accordance with claim 1 in which $R^1$ is H, $R^2$ is H, and $R^3$ is H; in which said compound is the hydrochloride salt thereof.

6. A compound in accordance with claim 1 in which $R^1$ is H, $R^2$ is H, and $R^3$ is NO.

7. A compound in accordance with claim 1 in which $R^1$ is H, $R^2$ is H and $R^3$ is $NO_2$.

8. A compound in accordance with claim 1 in which $R^1$ is NO, $R^2$ is H, and $R^3$ is $NO_2$.

9. A compound in accordance with claim 1 in which $R^1$ is $NO_2$, $R^2$ is H, and $R^3$ is $NO_2$.

10. A compound in accordance with claim 1 in which $R^1$ is $NO_2$, $R^2$ is $NO_2$, and $R^3$ is $NO_2$.

* * * * *